United States Patent [19]
Groch et al.

[11] 3,982,128
[45] Sept. 21, 1976

[54] DUAL CRYSTAL SCINTILLATION PROBE
[75] Inventors: Mark W. Groch, Mount Prospect; Frank R. Whitehead, Arlington Heights, both of Ill.
[73] Assignee: G. D. Searle & Co., Skokie, Ill.
[22] Filed: Mar. 17, 1975
[21] Appl. No.: 559,227

[52] U.S. Cl. .............................. 250/363 S; 250/367; 250/368
[51] Int. Cl.² .......................................... G01T 1/20
[58] Field of Search ................. 250/363 S, 367, 368

[56] References Cited
UNITED STATES PATENTS
3,793,519  2/1974  Mallard et al. .................. 250/363 S
3,899,675  8/1975  Floyd .............................. 250/363 S Primary Examiner—Archie R. Borchelt
Attorney, Agent, or Firm—Walter C. Ramm; Peter J. Sgarbossa; Albert Tockman

[57] ABSTRACT

A scintillation probe employing two scintillation detectors having partially overlapping fields of view. The overlapping fields of view allow radioactive events from a particular spatial region to be identified and tabulated separately. Preferably, one crystal is annularly positioned with respect to the other and is collimated so that radioactive events from the left ventricle of the human heart can be isolated to a large extent from simultaneous background. Useful cardiac information is obtained in a non-invasive technique of medical examination of living patients requiring only a single injection of a radioisotope.

15 Claims, 6 Drawing Figures

DUAL CRYSTAL SCINTILLATION PROBE

The present invention relates to a scintillation probe employing a plurality of scintillators having partially overlapping fields of view for use in medical testing to ascertain cardiac related measurement parameters.

BACKGROUND OF THE INVENTION

In the medical diagnosis and treatment of various heart ailments, it is highly advantageous for a cardiologist to obtain certain information related to the function and physical condition of the parts of the heart of a patient. The use of nuclear medicine, that is, the administration of a dosage of radioactive material for the purpose of tracing the path or volume of circulatory flow, has for some time been a potential source of such information. This information is typically presented to the attending physician as a radiocardiogram, or RCG, in the form of a tracing by a strip chart recorder. However, existing techniques for obtaining the measurements of cardiac parameters of interest have heretofore involved serious drawbacks. For the most part, such techniques require a catheter to be inserted into the heart or into a vein near the heart of a living patient in order to introduce a bolus of radiopharmaceutical into the heart of the patient under study. The risk of moving a seriously ill heart patient to the catherization laboratory of a hospital and the trauma of inserting a catheter into a vein of the patient has for the most part proven a sufficient deterrent to obtaining the patient data available with an RCG. Furthermore, tradition methods for otaining cardiac dynamic parameters have required insertion of a catheter into the heart followed by injection of dense contrast material and subsequent fluoroscopy. The procedure is time consuming with a certain amount of morbidity associated with the injection of the dense dye material which may cause cardiac arythmias and even change the dynamic parameters of the heart. In addition, the process has heretofore been unduly time consuming since the time required for development of X-rays to precisely locate the patient's heart in order to thereafter obtain meaningful measurements, as is currently the practice, is approximately 45 minutes. Moreover, with existing techniques it has been impossible to obtain all of the required patient data from a single injection of a radioisotope, so that sequential injections of separate dosages of radioisotopes have by necessity been employed. This further lengthens the process of obtaining a RCG. Furthermore, required corrections to one measurement are made on the basis of complementary measurements taken with respect to a different sample of a radioisotope at a different time. Because of inconsistencies in radioisotope injection techniques, heart rate fluctuations, and circulatory variations, the corrected measurements obtained from the RCG may not consistently represent an accurate picture of the various patient cardiac parameters measured.

Despite these various difficulties, there have been attempts to employ various instruments to measure cardiac parameters of patients. One such technique employing a scintillation camera is described in an article authored by Donald Van Dyke, et al, entitled "Cardiac Evaluation from Radioisotope Dynamics," Journal of Nuclear Medicine, Vol. 13, No. 8, pp. 585-592 (1972). This technique was non-invasive in nature, but the results obtained were not of a quality which would provide data of sufficient reliability to form the basis of cardiac diagnosis without the complementary use of invasive techniques. Also, the technique was time consuming in that six hours were required to evaluate all the data for one patient. The count rate proved to be quite low, so that the statistics which provide the basis for the calculations were inherently poor. In this procedure, regions of interest had to be set and results were operatordependent to that extent.

Another technique for obtaining an RCG employing a single crystal scintillation probe is described in an article by Peter P. Steele et al, "Simple and Safe Bedside Method for Serial Measurement of Left Ventricular Ejection Fraction, Cardiac Output, and Pulmonary Blood Volume," British Heart Journal, Vol. 36, pp. 122-133, 1974. This technique requires injection of a bolus of radioactivity by means of a central venous catheter, and is to this extent invasive. In addition, this method requires two sequential injections of doses of the radiopharmaceutical used.

The chamber of greatest interest to cardiologists is the left ventricle, the chamber responsible for supplying blood to the systemic circulation. A probe positioned over the left ventricle provides high frequency data on the left ventricle as well as cardiac output. Since a probe positioned over the left ventricle, by reason of the geometric positioning of the heart chambers within the body, partially views the right heart, pulmonary information can be obtained. However, this viewing of the right heart necessitates a correction for "crosstalk" or background in the analysis of the action of the left ventricle. The derivation of the necessary correction has heretofore not been straightforward. To the contrary, it has been quite complicated and has led to measurements inconsistent with or inconclusive with respect to the techniques employing other conventional instruments. The technique, as practiced by Steele and as described in the aforementioned article in the British Heart Journal, has had fair correlation with contrast angiography, however.

SUMMARY OF THE INVENTION

In contrast, the present invention provides the cardiologist with a nuclear probe which, with a single jugular injection of a bolus of radioisotope, can furnish the required cardiac parameters at bedside. This instrument allows the physician to obtain all measurements required during a single measurement cycle and eliminates any variations in measurements which might result from inconsistent injection techniques, variations in heart rate, and variations in probe positioning. Such distortions are inevitably present in systems which employ sequential measuring cycles.

It is an object of the present invention to provide an instrument for cardiac diagnosis which can effectively and consistently provide reliable corrections to data obtained to derive measurements of left ventricle function. This instrument enables the effective isolation of data from the left ventricle in a much more reliable manner than has heretofore been possible with other instruments.

It is furthermore an object of the present invention to provide a cardiac scintillation probe which may be employed to gather cardiac related data with the injection of a single dose of radioactive material. The "after the fact" background correction of prior techniques is theoretically poor, and it is believed that the present invention represents an improvement in this regard.

It is a further object of the invention to provide meaningful cardiac data complete with correction information which correction information is obtained without resorting to calculations or other modification of the raw data to obtain the measurements desired.

In one broad aspect of this invention, there is provided a scintillation probe for detecting and measuring radiation comprising transducer means including a plurality of separate and optically isolated scintillators within each of which light emissions are generated in response to impinging radiation, photodetector means in optical communication with said scintillators to generate electrical signals separately for each scintillator in reponse to detected light emissions, tabulating means for tabulating the aforesaid electrical signals, and collimating means defining partially overlapping fields of view for each scintillator to thereby allow electrical signals derived from radioactive events occurring within a specific spatial region of interest to be isolated for tabulation.

In another broad aspect, the scintillation probe of this invention may include a transducer having a central radiation receiving surface from which associated signals are generated in response to radiation incident thereon, a peripheral radiation, receiving surface encircling said central radiation receiving surface and from which associated signals are generated in response to radiation incident thereon which signals are distinguishable from signals associated with said central radiation receiving surface, tabulating means for separately tabulating the signals associated with said central and said peripheral radiation receiving surfaces, and collimating means defining a generally conical spatial region of acceptance centered on said central radiation receiving surface and further defining a cylindrical absorption region of space coaxial with respect to the aforesaid conical region wherein radiation emanating from said conical region and directed at said central radiation receiving surface is not absorbed by said collimating means and radiation emanating from said cylindrical region and directed at said peripheral radiation receiving surface is absorbed by said collimating means.

BRIEF DESCRIPTION

The nature of the invention may be more readily ascertained by reference to the accompanying drawings in which FIG. 1 is an elevational view of an instrument constructed according to this invention;

DETAILED DESCRIPTION

Figure 1:
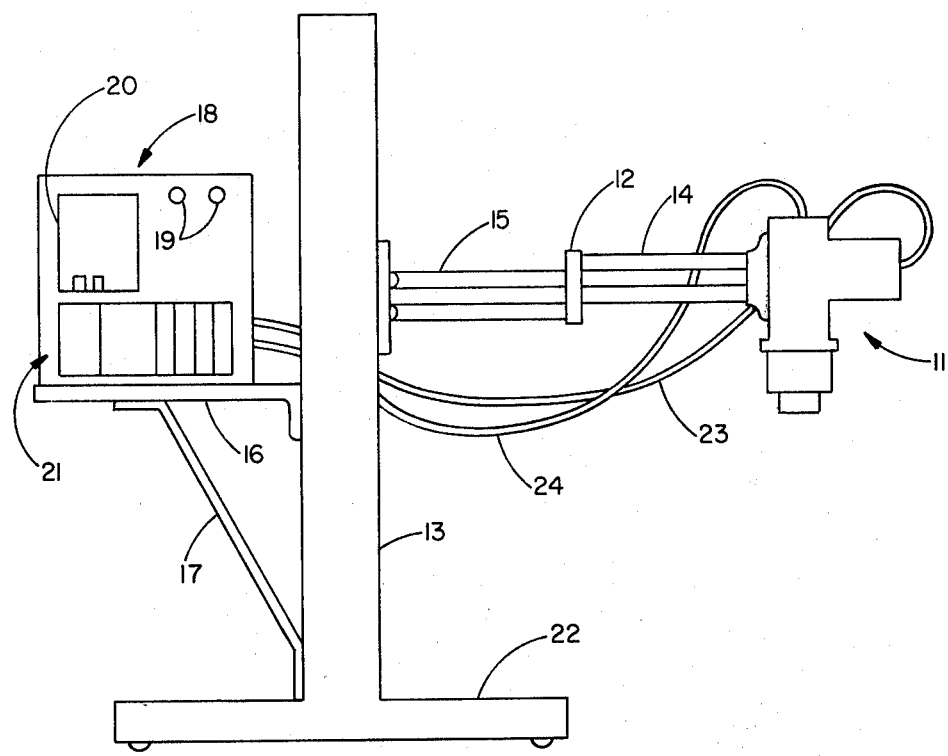

Referring now to FIG. 1 there is illustrated a scintillation counting instrument employing a stand having a base 22 and an upright standard 13. To the standard 13 is fastened a cantilevered arm consisting of two sections 15 and 14 joined by hinge 12. A scintillation probe 11 is attached to the end of the cantilevered section 14. Electrical connectors 23 and 24 connect the probe 11 to an electronic processing unit 18. The electronic processing unit 18 is arranged on a shelf 16 extending from the standard 13 and is supported by a brace 17. The electronic processing unit includes controls 19, pulse processing circuitry located in the plug-in electronic modules 21, and a tabulating means 20 in the form of an optical strip chart recorder. The recorder illustrated is an optical strip chart recorder with a frequency response of up to 120 hertz. The maximum frequency that will ever be needed is 180 beats per minute or 3 hertz, but to assure completely accurate recording of high frequency cardiac data (dicrotic notch, etc.) an optical strip chart recorder is preferred. It should be noted that a pen recorder may be sufficient.

Figure 2:
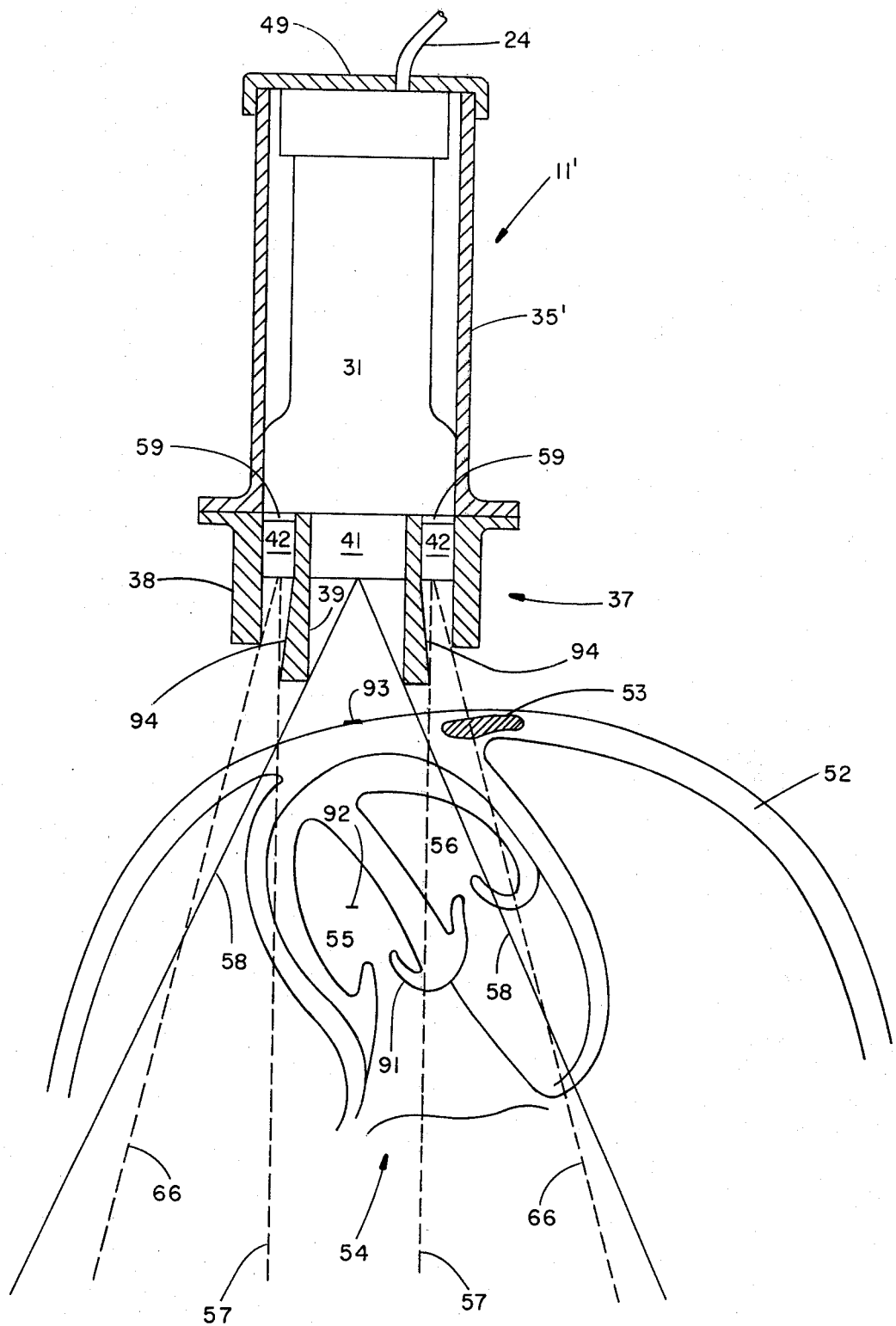
FIG. 2 is a sectional view of one embodiment of the scintillation probe of this invention.

The scintillation probe 11' of FIG. 2 is illustrated in a measuring position adjacent to the chest of a patient. FIG. 2 includes a transverse sectional view of the patient at chest level. The posterior rib cage 52 and sternum 53 are illustrated as are the right ventricle 56 and the left ventricle 55 of the heart 54 of the patient. The scintillation probe 11' includes a casing 35' positioned about a photomultiplier tube 31. An electrical cable 24 extends through an end-cap 49 from the preamplifier section of the photomultiplier tube 31. A central scintillation crystal 41 formed of thallium-activated sodium diode is laterally encircled by an annular peripheral scintillator 42, similarly formed of thallium-activated sodium iodide. The peripheral scintillator 42 is optically isolated from the central scintillator 41 by an annular interior lead collimator 39. The annular collimator 39 and an outer annular lead collimator 38 together form a collimating means 37. As illustrated, the inner collimator 39 absorbs radiation directed at the central scintillator 41 from within a first range of directions anywhere except within the conical spatial region of acceptance lying between the solid lines 58. The outer collimator 38 and the inner collimator 39 together absorb radiation directed at the peripheral scintillator 42 from within a second range of directions including all of those directions which lie outside of the spatial region of acceptance defined between the dashed lines 66 and 57 in FIG. 2. As can be seen, this second range of directions within which radiation is absorbed is different from and partially overlaps the first range. Similarly, the regions of acceptance for the central scintillator 41 and the peripheral scintillator 42 partially overlap. With this configuration of the collimator means 37 radiation originating or emanating from the cylindrical volume or region of space lying within the dashed lines 57 and directed at the peripheral scintillator 42 is absorbed by the collimator 39. Thus the spatial region of acceptance of the peripheral scintillator 42 is of a generally conical shape but with a central cylindrical core containing the cone axis removed.

Both of the scintillators 41 and 42 are optically coupled to the photodetector 31. Scintillations from the peripheral scintillator 42 must pass through an annular disc 59 formed of a light absorbing material. The heights of electrical pulses generated by the photodetector 31 in response to scintillations from the peripheral scintillator 42 are thereby reduced to a uniform extent so that they may be distinguished from pulses generated in response to scintillations occurring in the central scintillator 41. The principle by which this form of light filtration can be used to identify the one scintillator from several possible scintillators within which a scintillation occurred is more fully explained in U.S. Pat. No. 3,859,525. In brief, however, it can be stated that the voltage amplitude of an electrical pulse generated by photomultiplier 31 from a scintillation 42 is only a fraction of the amplitude of a pulse generated in response to a scintillation by scintillator 41 for scintillations of equal intensity. This is because the light from scintillator 42 is optically attenuated by the filter 59. Therefore, the scintillator associated with a particular voltage pulse is identified by the amplitude of that voltage pulse. Voltage pulses from photomultiplier tube 31 are transmitted by means of an electrical connection 24 to electrical circuitry for separately tabulating scintillations occurring in the central scintillator and scintillations occurring in the peripheral scintillator in the manner fully set forth in the foregoing U.S. Patent.

Figure 3:
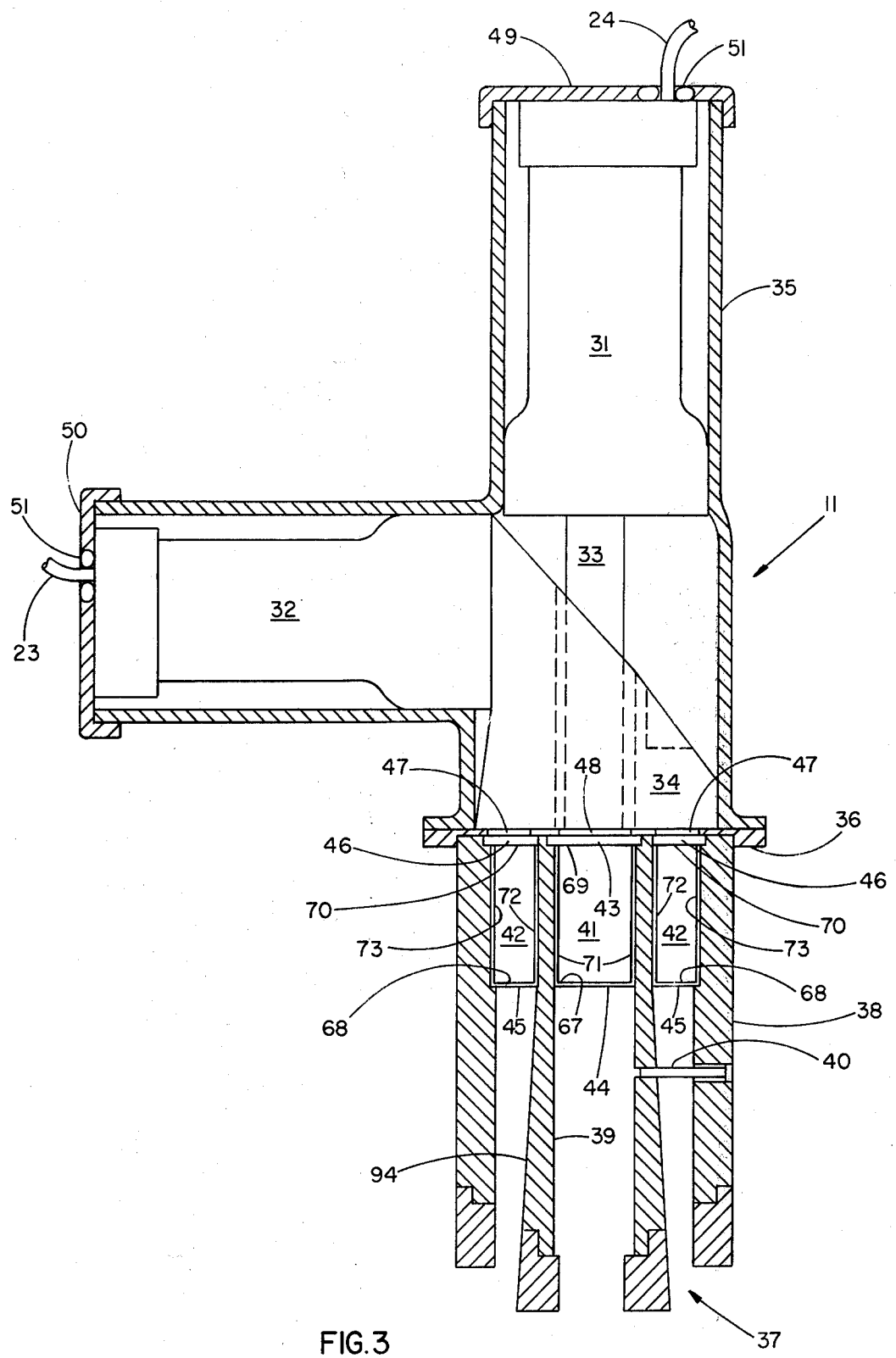
FIG. 3 is a sectional view of another embodiment of the scintillation probe of this invention.

An alternative form of a scintillation probe for detecting and measuring radiation in accordance with this invention is illustrated in FIG. 3. In this embodiment, the probe 11 includes a central scintillator 41 and a peripheral scintillator 42 as in the probe 11'. The scintillator 41 and 42 are both formed of thallium-activated sodium iodide and are encapsulated by aluminum containers 44 and 45 which are respectively secured to glass members 43 and 46. The central scintillator 41 has parallel ends 67 and 69 with perpendicular walls 71 extending therebetween to form a right cylindrical structure. The peripheral scintillator 42 has parallel ends 68 and 70 with perpendicular cylindrical walls 72 and 73 extending therebetween to encircle or envelope the walls 71 of the central scintillator 41 in a lateral direction. The peripheral radiation receiving surface 68 thereby encircles the central radiation receiving surface 67. Again, the aluminum containers 44 and 45 along with the central annular collimator 39 provide an optical barrier interposed between the central scintillator 41 and the peripheral scintillator 42. Likewise, the collimators 38 and 39 restrict in diverse fashion the direction from which radiation may impinge upon the ends of the central scintillator 41 and the peripheral scintillator 42.

In the embodiment of FIG. 3 a plurality of photodetectors 31 and 32 are provided. Each of these photodetectors generates electrical pulses in response to incident light scintillations. The photomultiplier tube 31 is optically coupled to the central scintillator 41 by means of the glass window 43, optical coupling compound 48, and a cylindrical light guide element 33. The photomultiplier 32 is optically coupled to the peripheral scintillator 42 by means of the annular glass window 46, a layer 47 of optical coupling compound, and the light guide element 34 designed in the geometrical shape indicated in FIGS. 3, 5, and 6. Light scintillations received by the light guide 33 are optically conducted to the photomultiplier 31. Light scintillations received by the light guide 34 from the scintillator 42 are directed, either by reflection or direct optical coupling, to the photomultiplier tube 32. In this embodiment, it can be seen that through its dual elements 33 and 34 the light guide is in optical communication with both the central scintillator 41 and the peripheral scintillator 42 and with the photodetectors 31 and 32 for directing light emanating from the scintillators into separate ones of the photodetectors. It should be noted here that an optical barrier exists between light guide elements 33 and 34. As illustrated, this optical barrier is air, although it could also be a solid material such as aluminum. The two elements 33 and 34 guide light only from their respective scintillators 41 and 42.

Figure 5:
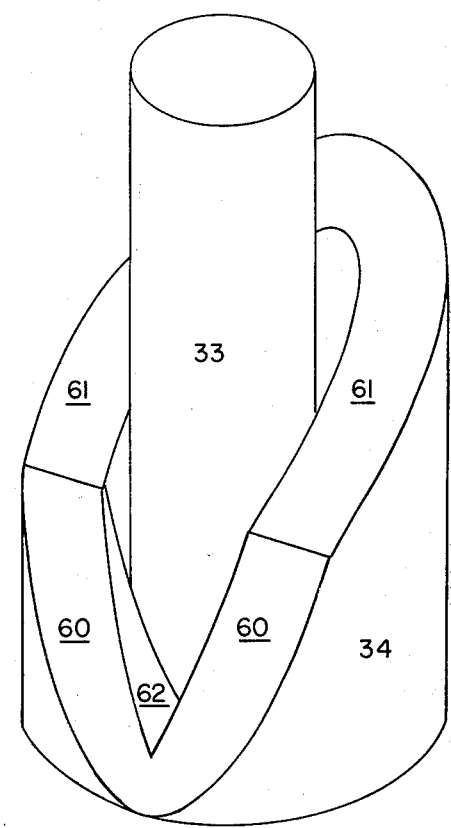
FIG. 5 is a perspective view of a light guide means employed in the embodiment of FIG. 3.
Figure 6:
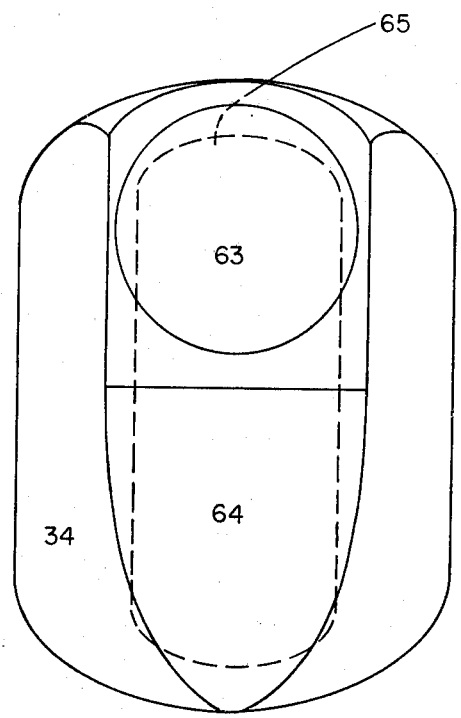
FIG. 6 is another perspective view of a portion of the light guide means of FIG. 5 viewed from a different position.

As is more clearly illustrated in FIG. 5, the light guide element 33 is comprised of a central right cylindrical transparent member, the ends of which are optically coupled to the central scintillator 41 and the photomultiplier tube 31. An annular cylindrical transparent element 34 is positioned to encompass the central element 33, but is optically isolated therefrom by an interstitial air space. That is, the light guide element 33 does not lie in contact with the interior walls of the light guide element 34. The light guide element 34 is geometrically shaped to provide total internal reflection into the photomultiplier 32. This is achieved by a construction in which the planar face 61 of light guide element 34 forms an angle of 45° with respect to the axis of the element 34. The planar face 60 lies at an angle of 21° with respect to a vertical line parallel to the axis of the element 34. Two surfaces 62 are planar surfaces lying at right angles to the surface 60, and together form a V-shaped notch in surface 60 wherein the angle at their mutual intersection is 44°. The photomultiplier 32 is designed to be positioned against the circular surface 63 in FIG. 6. A planar surface 64 lies at an angle of 10° with respect to the axis of the annular element 34. An interior cylindrical wall 65 defines a cylindrical aperture through the center of the element 34.

The interior annular collimator element 39 of the collimator device 37 serves to limit the field of view of the central scintillator 41 primarily to the left ventricle while the outer taper of the wall 94 of collimator element 39 helps to eclipse the left ventricle from the peripheral detector 42. The outer annular collimator element 38 restricts the field of view of the peripheral scintillator 42 distal to the left ventricle. Thus the unitized collimator device 37 allows the central scintillator 41 to view the left ventricle 55 plus some non-left ventricle background, while the peripheral scintillator 42 eclipses the left ventricle 55 and views the area providing a background contribution in the central scintillator 42, most notably the right ventricle 56.

As indicated in FIG. 3, the two annular components 38 and 39 of the collimator 37 are held rigidly together by steel screws 40 tapped into tungsten inserts in the annular rings 38 and 39. The tungsten inserts, which are epoxied into the lead collimator rings, provide hard metal for tapping the screws, and also serve to reduce the penetration of gamma rays along a path through the steel. The three steel supporting screws absorb an insignificant number of gamma rays in comparison to the total number of gamma rays collected by the peripheral scintillator 42, and hence do not affect uniformity in count rate around the annulus.

As previously discussed, the collimator means 37 defines channels delimiting different directional spatial regions from which radiation is allowed to impinge upon the central and the peripheral scintillators 41 and 42 respectively.

Figure 4:
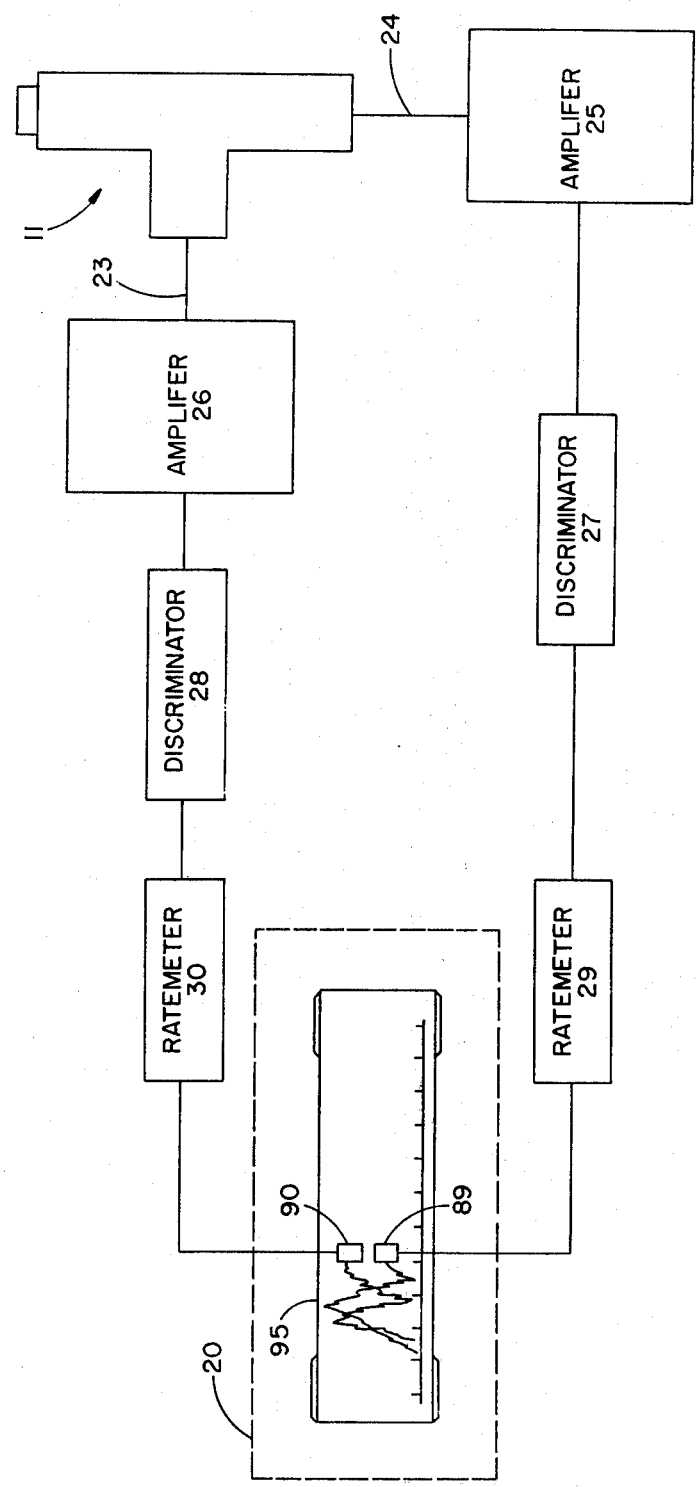
FIG. 4 is a block diagram of an embodiment of the invention.

FIG. 4 illustrates the pulse processing circuitry which is connected to the scintillation probe 11 for separately tabulating electrical pulses generated in the photomultipliers 31 and 32 in response to scintillations occurring in the central scintillator 41 and the peripheral scintillator 42. The electrical cable 24 is connected from the photomultiplier 31 to an amplifier 25, which in turn is connected to a discriminator circuit 27, to eliminate all pulses below a predetermined amplitude. The discriminator 27 in turn is connected to a ratemeter 29 which governs the fluctuations of a galvonometer 89 on the strip 95 of the optical recorder 20. Fluctuations in the ratemeter 29 produce fluctuations in the galvonometer 89 which deflects a light beam generating a strip chart recording on light sensitive paper. As stated before, however, recorder 20 need not be an optical pen recorder. In the same manner, the photomultiplier 32 is connected to an electrical cable 23 to an amplifier 26 and in turn to a discriminator 28. The discriminator 28 is connected to a ratemeter 30 which controls the operation of the galvonometer 90 on the strip 95 in the recorder 20. The strip chart recorder may be one of several available commercial units. One suitable recorder is manufactured by the Honeywell Company, Model 1508A - optical.

In the operation and utilization of the cardiac probe depicted, the mid-point of the left ventricle 55 must first be located. This is accomplished in a non-invasive manner through the use of T-scanning ultrasound. Techniques of obtaining ultrasonic measurements from the left ventricle of a patient are discussed in an article by Dr. Harvey Feigenbaum, "Echocardiographic Examination of the Left Ventricle," *Circulation*, Vol. 51, No. 1, January 1975. Using the mitralvalve 91 as a guide, the echogram generated by the ultrasound probe is used to locate the midpoint 92 of the left ventricle and a felt pen is used to mark the location 93 on the patient's chest, where the probe center is aligned with the left ventricle. The probe 11 or 11' is then positioned over this mark and a single injection of technetium 99m is given into the jugular vein of the patient. A one millicurie dose of technetium 99m is sufficient. As the injection is given, the scintillation counting system is activated and optical beams 89 and 90 trace the left ventricle and background responses respectively on the moving strip 95. The probe is typically maintained in position for a time period sufficient for the bolus to become uniformly distributed throughout the entire blood volume. Equilibrium is thereby established so that a uniform level of radioactivity exists throughout the circulatory system, whereby blood volume measurements are obtained to calibrate the curve to determine cardiac output. True equilibrium is established in 8-10 minutes. Data on the left ventricle is obtained only from the left ventricle on a beat to beat basis during the first pass, during which period about 10 beats are usable. First recirculation is noted for timing recirculation only, as one recirculation time is necessary. The several measurements are taken primarily to determine blood recirculation time of the patient. As previously discussed, the collimator means 37 defines channels delimiting differential directional spatial regions from which radiation is allowed to impinge upon the central and the peripheral scintillators 41 and 42 respectively.

The foregoing detailed description and illustrated embodiments of the invention are given by way of example only, as numerous variations in the geometry of the collimator, scintillation detectors, light pipes, and other configurative variations of these components and of the electrical circuitry and photodetectors associated therewith will be readily apparent to those skilled in the art.

We claim:

1. A scintillation probe for detecting and measuring radiation comprising transducer means having a central radiation receiving element from which associated signals are generated in response to radiation incident thereon, a peripheral radiation receiving element encircling said central radiation receiving element and from which associated signals are generated in response to radiation incident thereon which signals are distinguishable from signals associated with said central radiation receiving element, tabulating means for separately tabulating the signals associated with said central and peripheral radiation receiving elements, and collimating means defining a generally conical spatial region of acceptance centered on a surface of said central radiation receiving element and further defining a cylindrical absorption region of space coaxial with respect to the aforesaid conical region wherein radiation emanating from said conical region and directed at said central radiation receiving element is not absorbed by said collimating means and radiation emanating from said cylindrical region and directed at said peripheral radiation receiving element is absorbed by said collimating means.

2. A scintillation probe for detecting and measuring radiation comprising: a central scintillator and a peripheral scintillator wherein said peripheral scintillator is optically isolated from and encircles said central scintillator, collimating means for absorbing radiation directed at said central scintillator from within a first range of directions and for absorbing radiation directed at said peripheral scintillator from within a second range of directions different from and partially overlapping said first range, photodetector means optically coupled to said central scintillator and said peripheral scintillator, and electrical circuitry for separately tabulating scintillations occurring in said central scintillator and scintillations occurring in said peripheral scintillator.

3. The scintillation probe of claim 2 wherein the walls of said peripheral scintillator are coextensive with the walls of said central scintillator.

4. The scintillation probe of claim 2 wherein said collimating means is comprised of a first annular element of radiation absorbent metal interposed between said central and peripheral scintillators and extending beyond at least one end of both said peripheral scintillator and said central scintillator to absorb radiation directed at said central scintillator from said first range of directions, and said collimating means is further comprised of a second annular element of radiation absorbent metal encircling said peripheral scintillator and extending beyond at least the aforesaid one end of said peripheral scintillator to absorb radiation directed at said peripheral scintillator.

5. The scintillation probe of claim 3 wherein said first annular element of said collimating means defines a generally conical region of space centered on an end of said central scintillator from within which radiation directed at said central scintillator is not absorbed, and said first annular element also absorbs radiation directed at said peripheral scintillator and emanating from a cylindrical region of space which region is coaxial with respect to the aforesaid conical region.

6. A scintillation probe for detecting and measuring radiation comprising a central scintillator and a peripheral scintillator both having ends and walls extending therebetween, and wherein the walls of said peripheral scintillator encircle the walls of said central scintillator, and further comprising an optical barrier interposed between said central scintillator and said peripheral scintillator, collimator means restricting in diverse fashion the directions from which radiation may impinge upon the ends of said central and said peripheral scintillators, a plurality of photodetectors which generate electrical pulses in response to incident light scintillations and different ones of which are optically coupled to said central scintillator and said peripheral scintillator, and electrical circuitry for processing separately pulses generated in response to scintillations in said central scintillator and scintillations in said peripheral scintillator.

7. The scintillation probe of claim 6 further comprising light guide means optically coupling said photodetectors and said central and said peripheral scintillator such that light scintillations received by said light guide means from said central scintillator and from said peripheral scintillator are directed to different ones of said plurality of photodetectors.

8. A scintillation counting instrument comprising:
a. central scintillator having parallel ends with perpendicular walls extending therebetween,
b. a peripheral scintillator having parallel ends with perpendicular walls extending therebetween to envelop the walls of said central scintillator,
c. an optical barrier interposed between said central scintillator and said peripheral scintillator,
d. collimator means defining channels delimiting different spatial regions from which radiation is allowed to impinge upon said central and said peripheral scintillators respectively,
e. separate photodetectors optically coupled to each of said central and peripheral scintillators,
f. light guide means in optical communication with both said central and said peripheral scintillators and with each of said photodetectors for directing light emanating from said scintillators into separate ones of said photodetectors, and,
g. pulse processing circuitry for separately tabulating electrical pulses generated in response to scintillations occurring in said central and said peripheral scintillators.

9. The scintillation counting instrument of claim 8 comprising a light guide means in optical communication with both said central and said peripheral scintillators and with each of said photodetectors for directing light emanating from said scintillators into separate ones of said photodetectors.

10. The scintillation counting instrument of claim 8 wherein said light guide means is comprised of a central right cylindrical transparent member, the ends of which are optically coupled to said central scintillator and a first photodetector, and an annular cylindrical transparent member positioned to encompass said central member in optical isolation therefrom, and geometrically shaped to provide total internal reflection into a second photodetector which is optically coupled thereto.

11. The scintillation counting instrument of claim 10 wherein said first and second members of said light guide are separated by an annular space to provide optical isolation of said members from each other.

12. In a scintillation counting instrument employing dual scintillators, the improvement wherein a peripheral scintillator is positioned concentrically about a central scintillator and said scintillators are separated from each other by an optical barrier, a separate photodetector is associated with each of the aforesaid scintillators, and a separate light guide element is provided in optical communication with each of said peripheral and central scintillators and in further optical communication with a single one of said photodetectors for directing light emanating from said scintillators into separate ones of said photodetectors.

13. The scintillation counting instrument of claim 12 wherein said light guide elements include a central right cylindrical transparent member, the ends of which are optically coupled to said central scintillator and a first photodetector, and an annular cylindrical transparent member positioned to encompass said central member in optical isolation therefrom, and geometrically shaped to provide total internal reflection into a second photodetector which is optically coupled thereto.

14. The scintillation counting instrument of claim 12 wherein said first and second light guide members are separated by an annular space to provide optical isolation of said members from each other.

15. A scintillation counting instrument comprising:
a. central scintillator having parallel ends with perpendicular walls extending therebetween,
b. a peripheral scintillator having parallel ends with perpendicular walls extending therebetween to envelop the walls of said central scintillator,
c. an optical barrier interposed between said central scintillator and said peripheral scintillator,
d. collimator means defining channels delimiting different spatial regions from which radiation is allowed to impinge upon said central and said peripheral scintillators respectively,
e. separate photodetectors optically coupled to each of said central and peripheral scintillators, and
f. pulse processing circuitry connected to said photodetectors for separately tabulating electrical pulses generated in response to scintillations occurring in said central and said peripheral scintillators.

* * * * *